United States Patent
Pratt

(10) Patent No.: US 10,444,071 B1
(45) Date of Patent: Oct. 15, 2019

(54) CALIBRATION TARGET FOR IMAGE SENSOR

(71) Applicant: Patricia D. Pratt, Redondo Beach, CA (US)

(72) Inventor: Patricia D. Pratt, Redondo Beach, CA (US)

(73) Assignee: NORTHROP GRUMMAN SYSTEMS CORPORATION, Falls Church, VA (US)

( * ) Notice: Subject to any disclaimer, the term of this patent is extended or adjusted under 35 U.S.C. 154(b) by 579 days.

(21) Appl. No.: 15/253,420

(22) Filed: Aug. 31, 2016

(51) Int. Cl.
| | |
|---|---|
| H04N 7/18 | (2006.01) |
| G01J 3/02 | (2006.01) |
| H04N 5/225 | (2006.01) |
| H04N 5/33 | (2006.01) |
| G01J 3/28 | (2006.01) |
| B64D 47/08 | (2006.01) |

(52) U.S. Cl.
CPC .......... *G01J 3/0297* (2013.01); *B64D 47/08* (2013.01); *G01J 3/2823* (2013.01); *H04N 5/2258* (2013.01); *H04N 5/332* (2013.01); *H04N 7/181* (2013.01)

(58) Field of Classification Search
CPC .................................................. G01J 3/0297
USPC ....................................................... 348/144
See application file for complete search history.

(56) References Cited

U.S. PATENT DOCUMENTS

| | | | |
|---|---|---|---|
| 4,511,229 A * | 4/1985 | Schwartz | G03B 27/735 396/225 |
| 5,036,435 A * | 7/1991 | Tokuda | G02B 6/001 362/554 |
| 5,311,272 A * | 5/1994 | Daniels | G01S 17/89 356/342 |
| 5,790,188 A * | 8/1998 | Sun | G01J 3/2823 348/143 |
| 7,298,869 B1 * | 11/2007 | Abernathy | G06K 9/0063 324/323 |
| 8,767,210 B1 | 7/2014 | Lukashin et al. | |
| 2011/0205536 A1 * | 8/2011 | Johnsen | G01J 3/06 356/326 |
| 2012/0292494 A1 * | 11/2012 | Silny | G01J 1/0414 250/252.1 |
| 2014/0300806 A1 * | 10/2014 | Pollock | H04N 5/2254 348/373 |
| 2016/0069741 A1 * | 3/2016 | Ritter | G01J 3/0297 356/402 |
| 2016/0232650 A1 * | 8/2016 | Christ | G06T 7/80 |

OTHER PUBLICATIONS

Rao, et al.: "*Post-Launch Calibration of Meteorological Satellite Sensors*"; Adv. Space Res. vol. 23, No. 8, pp. 1357-1365, 1999.

* cited by examiner

*Primary Examiner* — Leron Beck
(74) *Attorney, Agent, or Firm* — Tarolli, Sundheim, Covell & Tummino LLP

(57) ABSTRACT

A calibration target for an image sensor can include a panel with a predetermined length and width. The calibration target can also include an optical fabric overlaying a surface of the panel that generates light on a predetermined spectral band corresponding to a spectral band detectable by the image sensor spaced apart from the calibration target by a predetermined distance. The generated light can have sufficient luminance to penetrate a predetermined depth of water and to saturate at least one pixel of the image sensor.

19 Claims, 4 Drawing Sheets

CALIBRATION TARGET FOR IMAGE SENSOR

TECHNICAL FIELD

This disclosure relates to a calibration target for an image sensor.

BACKGROUND

Meteorological satellites operating in geostationary orbits around the Earth provide observations of the Earth's surface and clouds. Images in or near the visible spectral domain can be used for the weather forecast and for monitoring important climate variables such as the surface insolation, surface albedo, pollution, smog and cloud characteristics. In some examples, such meteorological satellites can employ an imager.

Calibrating imagers is a common pre-processing step for remote sensing analysts that need to extract data and create scientific products from images. Calibration attempts to compensate for radiometric errors from sensor defects, variations in scan angle, and system noise to produce an image that represents true spectral radiance at the sensor.

SUMMARY

One example relates to a calibration target for an image sensor that can include a panel with a predetermined length and width. The calibration target can also include an optical fabric overlaying a surface of the panel that generates light on a predetermined spectral band corresponding to a spectral band detectable by the image sensor spaced apart from the calibration target by a predetermined distance. The generated light can have sufficient luminance to penetrate a predetermined depth of water and to saturate at least one pixel of the image sensor.

Another example relates to a system for calibrating an image sensor that includes a floatation device and a calibration target affixed to the floatation device. The calibration target can include a plurality of panels arranged to provide a predetermined length and a predetermined width of the calibration target. The calibration target can also include a plurality of sheets of optical fabric. Each of the plurality of sheets of optical fabric overlays a corresponding one of the plurality of panels. Each of the plurality of sheets of optical fabric can generate light on a predetermined spectral band corresponding to a spectral band detectable by the image sensor spaced apart from the calibration target by a predetermined distance. The light generated by the plurality of sheets of optical fabric has an aggregate sufficient luminance to penetrate a predetermined depth of water and to saturate at least one pixel of the image sensor.

Yet another example relates to a calibration target for an image sensor that can include a plurality of sheets of fiber optic fabric that each generates light to provide light on spectral band detectable by the image sensor. The generated light has sufficient luminance to penetrate one meter of water and to saturate at least one pixel of the image sensor.

DETAILED DESCRIPTION

Examples described herein relate to a calibration target for calibrating an image sensor operating on an aircraft or a satellite. The calibration target can be formed of a panel with a sheet of optical fabric overlying a surface of the panel. The sheet of optical fabric can generate light in a spectral band(s). Aircraft and/or satellites with the image sensor mounted thereon can be configured to fly-over the calibration target such that pixels of the image sensor can simultaneously capture a sample of the spectral band(s). The samples captured of the spectral band(s) can be used to calibrate the image sensor to compensate for errors caused, for example, by environmental conditions, atmospheric variables (e.g., airborne dust, water zone vapor, etc.) and/or atmospheric attenuations.

The calibration target can be submerged in water and anchored at a relatively stationary position. In some examples, the calibration target can be configured to change colors of illumination (e.g., change spectral bands). Such change of colors can be employed to increase accuracy of the calibration of the image sensor and/or be employed in functional typing of a species of aquatic life (e.g., phytoplankton).

Figure 1:
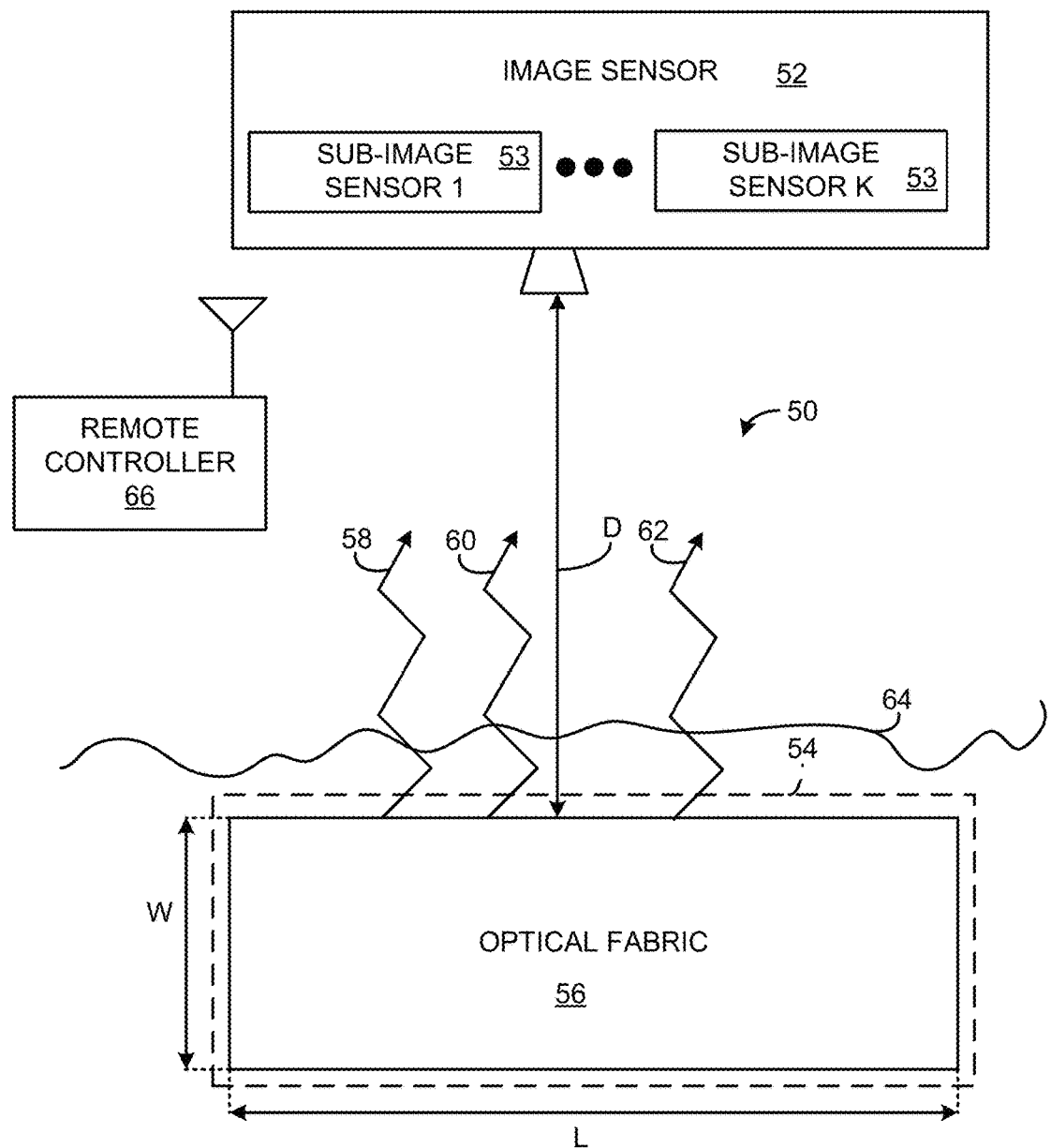
FIG. 1 illustrates an example of a system for calibrating an image sensor.

FIG. 1 illustrates an example of a system 50 for calibrating an image sensor 52. The image sensor 52 can be an airborne imager. For instance, the image sensor 52 can be deployed on an aircraft or a satellite. The image sensor 52 can be configured to receive electromagnetic (EM) waves in up to about 10 spectral bands. In some examples, the image sensor 52 can include K number of sub-image sensors 53, with outputs that are aggregated to form an input of the image sensor 52, where K is an integer greater than or equal to one. In such a situation, each of the sub-image sensors 53 can be single band image sensors.

The image sensor 52 can be configured to capture images of a given area. In examples where the image sensor 52 is affixed to an aircraft or satellite, the given area can be a specific geographic area of the Earth. In some examples, the specific geographic area can include land and/or water.

Due to environmental variables (e.g., change of temperature, vibrations, etc.), the image sensor 52 may need calibration on a periodic and/or as-needed (e.g., ad-hoc) basis. In such a situation, the image sensor 52 can be configured to capture an image of a calibration target 54. The calibration target 54 can have a predetermined size, color and functional characteristics that can be relied upon by the image sensor 52 to facilitate calibration.

The calibration target 54 can be a panel or a plurality of panels (e.g., a frame) with a predetermined length (labeled and FIG. 1 as "L") and a predetermined width (labeled in FIG. 1 as "W"). In some examples, calibration target 54 can have a square or rectangular shape. In other examples, the calibration target 54 can be circular or hexagonal dependent upon specifications and requirements as well as sampling pattern of the image sensor 52. For instance, an image sensor 52 deployed on an aircraft can have the ability to sample the calibration target 54 on a task plan that includes frequent overpasses while an image sensor 52 deployed on a satellite may have limited daily viewing times.

The calibration target 54 can have an optical fabric 56 that can overlay the panel. In examples where the calibration target 54 includes a plurality of panels, multiple sheets of optical fabric 56 can overlay individual panels, as described herein. The optical fabric 56 itself can have a plurality of warp and weft threads to provide a plurality of spectral capabilities. For instance, the illuminance of warp threads can be on one individual control system (e.g., a circuit) with a specific color or set of colors while the weft threads would be on a similar but separate control system (e.g., another circuit). The predetermined width and length of the calibration target 54 can depend on a distance (labeled in FIG. 1 as "D") between the image sensor 52 and the calibration target 54. The distance between the image sensor 52 and the calibration target 54 can be between about 1 kilometer (wherein the image sensor 52 is mounted on an aircraft) and 400 kilometers (wherein the image sensor 52 is mounted on a satellite). The predetermined width and the predetermined length of the calibration target 54 can be selected, for example, based on an area viewable by the image sensor 52 that corresponds to a single pixel of the image sensor 52. Accordingly, the predetermined width and the predetermined length of the calibration target 54 can have a minimum size corresponding to the area viewable by a single pixel in the image sensor 52.

The calibration target 54 can be sized and/or illuminated in a manner that the image sensor 52 can capture a measurable quantity of light of at least 7.9 photons per every 91 meters (about 300 feet) of the distance D between the image sensor 52 and the calibration target 54 if the image sensor 52 is traveling at a high velocity (e.g., such as in a satellite moving at a rate of about 7000 m/s). In situations where the image sensor 52 is traveling slower, the image sensor 52 may be able to operate properly while capturing a higher number of photons per 91 meters of the distance D from the longer dwell time or lower altitude. Such illumination can be generated at the optical fabric 56 of the calibration target 54.

In a situation where the image sensor 52 is mounted on an aircraft, each pixel of the image sensor 52 can correspond to an area size of at least 5 meters (m) by 5 meters. Accordingly, in such a situation, the predetermined width and the predetermined length of the calibration target 54 can be about 5 m or more, such that the calibration target 54 has an area of at least about 25 square meters ($m^2$) or more. In situations where the image sensor 52 is mounted on a satellite, each pixel of the image sensor 52 can correspond to an area size of at least 250 m by 250 m. Accordingly, the predetermined length and the predetermined width can be about 250 m, such that the calibration target 54 has an area of at least about 62,500 $m^2$. Moreover, although the examples described have the predetermined width and length of the calibration target being equal (e.g., to form a square), in some examples, the predetermined width and the predetermined length of the calibration target 54 can be different (e.g., to form a rectangle). As noted, the size of the calibration target 54 can be proportional to the predetermined approximate distance, D of separation between the image sensor 52 and the calibration target 54. That is, the larger the predetermined approximate distance, D of separation between the image sensor 52 and the calibration target 54, the larger the calibration target 54 may be.

The optical fabric 56 of the calibration target 54 can be formed as a textile with interwoven threads of material. In some examples, the optical fabric 56 can be a sheet of fiber optic fabric. The optical fabric 56 may be an active component that is illuminated with a powered light source optically coupled to edges of the optical fabric 56. In other examples, the optical fabric 56 can be a fiber optic filament, or other synthetic fabric (e.g., polyester) or natural fabric (e.g., cotton fabric) with illumination sources, such as light emitting diodes (LEDs) mounted thereon.

The optical fabric 56 can output visible light rays with a specific radiance. In particular, the light waves output by the optical fabric 56 can be a single color or a mix of colors on a predetermined set of spectral bands (e.g., a single spectral band or a plurality of spectral bands). The light rays output by the optical fabric 56 are depicted in FIG. 1 as arrows 58, 60 and 62. The predetermined set of spectral bands can correspond to the spectral bands detectable by the image sensor 52.

The calibration target 54 can be deployed in a body of water represented as reference number 64. The body of water 64 can be, for example, an ocean, sea or lake. In some examples, the calibration target 54 can be submerged in about 4 centimeters (cm) to about 1 m of water. In some examples, the calibration target 54 can be anchored to a floor of the body of water 64 and the panel on which the optical fabric 56 is attached can operate as a buoy to maintain submergence of the calibration target 54. In other examples, the calibration target can be affixed to a floatation device to maintain submergence of the calibration target 54 into the body of water 64.

The image sensor 52 can capture/sample a portion of the light rays 58, 60 and 62 emitted by the optical fabric 56. The light output by the calibration target 54 (indicated by the light rays 58, 60 and 62) can have sufficient luminance (e.g., brightness) to saturate at least one pixel of the image sensor 52. Moreover, since the wavelengths and frequencies radiated from the optical fabric 56 are predetermined and can be programmed into the image sensor 52, the image sensor 52 can be calibrated. The calibration of the image sensor 52 can compensate for errors/drift caused by environmental conditions (e.g., temperature), atmospheric variables (e.g., airborne dust, water zone vapor, etc.) and/or atmospheric attenuations.

The calibration target 54 can be controlled by a remote controller 66. The remote controller 66 can be representative of one or more computing devices. The remote controller 66 can communicate wirelessly with the calibration target. For example, the calibration target can include a (local) controller that can communicate wirelessly with the remote controller 66 to control an output of the optical fabric 56. Additionally, the remote controller 66 can communicate with the image sensor 52 to initiate a calibration procedure.

As noted, in some examples, the image sensor 52 can include the K number of sub-image sensors 53 that each detects a different, single, spectral band of light. For instance, in such a situation, the image sensor 52 could include 3 sub-image sensors 53 that detect red, blue and green light, respectively. In this situation, during a calibration procedure, the output of the optical fabric 56 can be changed periodically and/or asynchronously to fine tune calibration of each of the plurality of sub-image sensors 53.

In one example, during a calibration procedure, the remote controller 66 can cause the optical fabric 56 to output a solid color in a particular spectral band to be detected by a particular sub-image sensor 53 of the image sensor 52. For example, the optical fabric 56 can output a red color and the sub-image sensor 53 of the image sensor 52 that detects red can be calibrated, which sub-image sensor 53 can be referred to as a red sub-image sensor 53. Additionally, in this situation, the remote controller 66 can cause the optical fabric 56 to output a blue color for the red sub-image sensor 53 of the image sensor 52. During this portion of the calibration, the amount of blue light detected by the red sub-image sensor 53 can be measured to determine an amount of "cross talk" corresponding to unwanted transfer of signal detected by the red channel noted as sub-image sensor 53.

In other examples, the calibration target 54 can be employed in a plant functional typing procedure for aquatic life. Each species of phytoplankton absorbs and transmits different light waves. Accordingly, the remote controller 66 can control the output of the optical fabric 56, which can cause the optical fabric 56 to output light at a predetermined wavelength, which can be shined through/on phytoplankton of a specific species similar to artificially controlling the bottom surface type. In such a situation, the image sensor 52 can detect and measure the amount of light and the wavelength of the light transmitted by the optical fabric 56 and through the phytoplankton. This measurement can be employed (e.g., by the remote controller 66 or another computing device) to determine the species of the phytoplankton, as well as the density of the phytoplankton in the water 64.

In some examples, the calibration target 54 can include a global navigation satellite system (GNSS) (e.g., a global positioning system (GPS) or GLONASS) receiver and transmitter for determining and reporting the location (e.g., latitude and longitude coordinates) of the calibration target 54 to the remote controller 66, which location can be relayed to the image sensor 52. In this manner, the image sensor 52 can capture an area that includes the calibration target 54 during calibration. Additionally, the remote controller 66 can cause the optical fabric 56 to output the light rays 58, 60 and 62 at times when the image sensor 52 is overhead and to cease outputting of light at other times to conserve power (e.g., battery power).

The calibration target 54 can be deployed in a permanent/semi-permanent location. The calibration target 54 can operate for long period of time with little to no maintenance. For example, in some deployments of the calibration target 54, only infrequent power management may be needed (e.g., battery replacement).

Figure 2:
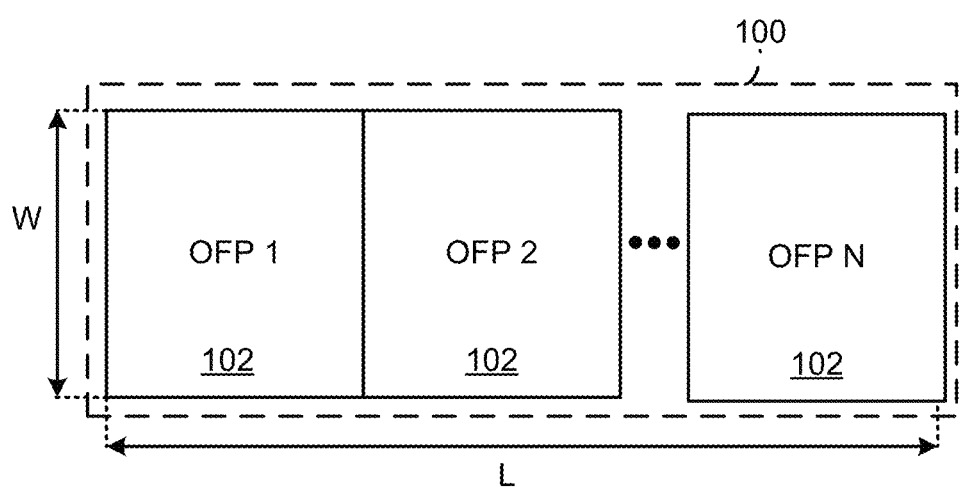
FIG. 2 illustrates an example of a calibration target for an image sensor.

FIG. 2 illustrates an example of a calibration target 100 that could be employed to implement the calibration target 54 of FIG. 1. The calibration target 150 can be formed from N number of panels 102 with optical fabric overlaying a side of the panel, which panels can be referred to as optical fabric panels 102 (labeled as "OFP" in FIG. 2), where N is an integer greater than or equal to one. The calibration target 100 can have a predetermined width (labeled in FIG. 2 as "W") and a predetermined length (labeled in FIG. 2 as "L"). Each of the N number of optical fiber panels 102 can form a portion of the total length and width of the calibration target 100. Moreover, in some examples, each of the N number of optical fabric panels 102 can be substantially the same size. Alternatively, in other examples, some (or all) of the N number of optic fabric panels 102 can have different sizes or shapes such has hexagons, which nest uniformly. In some examples, the calibration target 100 can be substantially square, with substantially equal predetermined width and a predetermined length, and in other examples, the calibration target 100 can be rectangular with an unequal predetermined width a predetermined length.

In operation, the calibration target can be submerged in about 4 cm to about 1 m of water. Moreover, the optical fabric panels 102 transmit light from an illumination source (e.g., fiber optic fabric or LEDs) over a predetermined set of spectral bands. The transmitted light can be captured/sampled by an image sensor (e.g., the image sensor 52 of FIG. 1) to facilitate calibration and/or functional typing of phytoplankton or other aquatic life.

Moreover, during operation, each of the N number of optical fiber panels 102 can output the same color or different colors. In situations where the N number of optical fiber panels 102 output different colors, an image sensor that employs the calibration target 100 to facilitate calibration (e.g., the image sensor 52) can detect the output of the optical fiber panels 102 as a single color since the colors aggregate, integrate and combine over the distance between the image sensor and the calibration target 150 (the distance 'D' illustrated in FIG. 1) similarly to natural and desired targets on the earth's surface of interest to the image sensor. Establishing a known source gives insight into the validation of real targets needed by the mission objectives.

Figure 3:
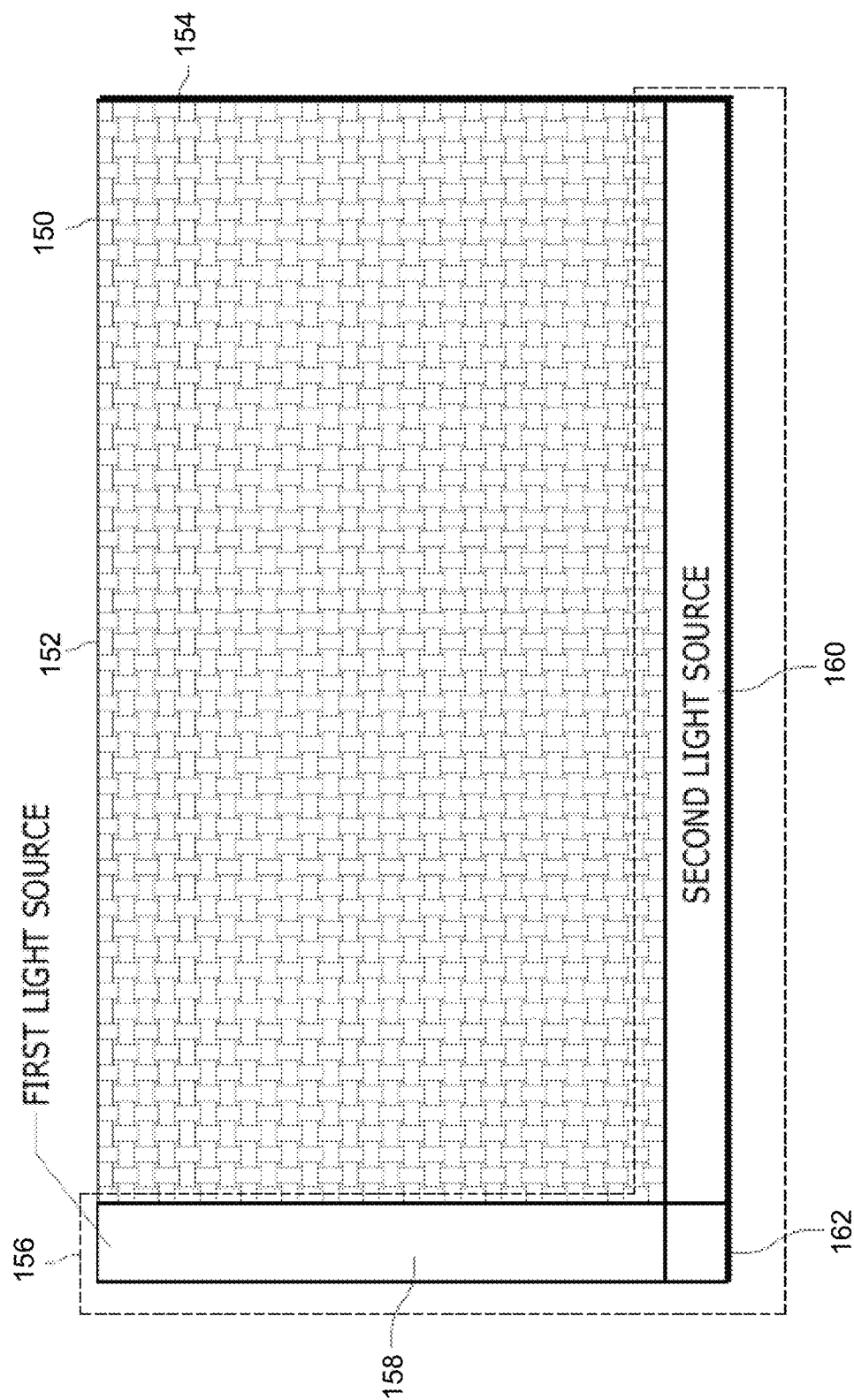
FIG. 3 illustrates an example of an optical fabric for a calibration target.

FIG. 3 illustrates a detailed view of an example of a sheet of optical fabric 150 that could be employed, for example, to implement the optical fabric 56 of FIG. 1 and or as the optical fabric of an optical fabric panel 102 of FIG. 2. The optical fabric 150 illustrated in FIG. 3 is implemented as a fiber optic fabric. Thus, the optical fabric 150 is formed from a plurality of interwoven optical fibers 152 and 154. The optical fibers 152 can extend in a first direction and the optical fibers 154 can extend in a second direction, normal (e.g., 90 degrees) from the first direction. The optical fabric 150 can also have a lighting system 156 that is in optical communication with the optical fabric 150 to illuminate the optical fabric 150. In the example illustrated in FIG. 3, the lighting system 156 can include a first light source 158 and a second light source 160. In other examples, more than two light sources could be employed. The first light source 158 can inject light in to the optical fibers 152 that extend in the first direction. The second light source 160 can inject light into the optical fibers 154 that extend in the second direction.

The lighting system 156 can include a controller 162 that controls the output of the first light source 158 and the second light source 160. The controller 162 can be implemented, for example as a microcontroller, an application specific integrated circuit chip (ASIC) or a microprocessor that executes machine readable instructions stored on a non-transitory machine readable medium (e.g., random access memory, volatile or non-volatile) and/or as a system-on-a-chip. In some examples, the controller 162 can include a network interface for wireless communication with an external source (e.g., the remote controller 66) of FIG. 10. Additionally or alternatively, the controller 162 can communicate with a controller of another sheet of optical fabric.

The controller 162 can change an output color of the optical fibers 152 and the optical fibers 154. Moreover, by synchronizing the change in output colors of the optical fibers 152 and the optical fibers 154 additional colors can be output by the optical fabric 150. For instance, if the first light source 158 injects a red color into the optical fibers 152 extending in the first direction, and the second light source 160 injects a blue color into the optical fibers 154 extending in the second direction the image sensor (e.g., the image sensor 52 of FIG. 1) would observe the sheet of optical fabric 150 as outputting a magenta color; however the respective spectral bands on the image sensor would be able to discriminate the exiting light.

As noted, the controller 162 can be in communication with an external source (e.g., the remote controller 66 or another optical controller) to control an output of the first light source 158 and the second light source 160 to finely tune/measure the image sensor during calibration. Additionally, as noted, the sheet of optical fabric 150 could be employed in an array of optical fiber panels (e.g., the calibration target 100 of FIG. 2). In such a situation, the external system can synchronize the output of the sheet of optical fabric 150 with the output of other sheets of fiber optic fabric in the calibration target.

In a similar manner, the controller 162 can be controlled to adjust an output color to facilitate functional typing of aquatic life (e.g., phytoplankton). In such a situation, the output of the sheet of optical fabric 150 can be controlled and/or synchronized with other sheets of fiber optic fabric in a calibration target.

Figure 4:
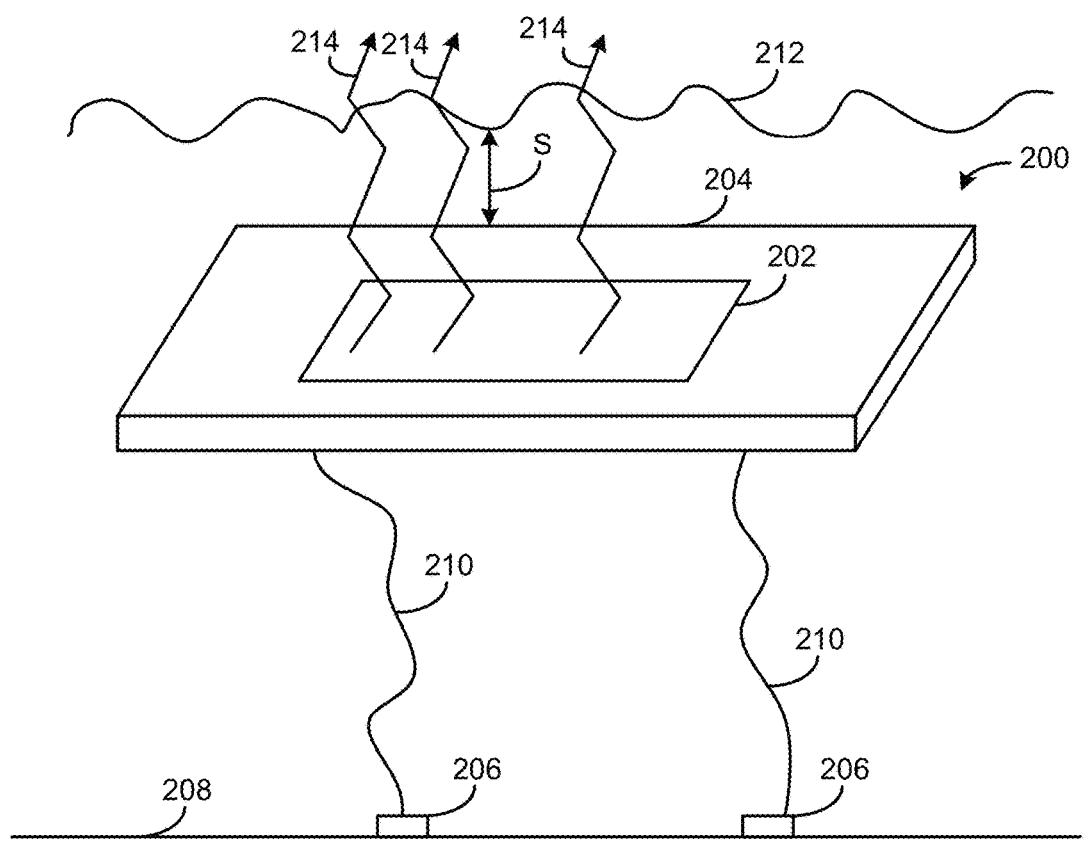
FIG. 4 illustrates a diagram of an example of a deployed calibration target for an image sensor.

FIG. 4 illustrates an example of a system 200 that includes a calibration target 202 that has been deployed for calibration of an image sensor and/or functional typing of aquatic life. The calibration target 202 can be employed to implement the calibration target 54 of FIG. 1 and/or the calibration target 100 of FIG. 2. The system 200 can be submerged in a body of water. For example, the system 200 can be deployed in saltwater (e.g., an ocean or a sea) or freshwater (e.g., a lake).

The calibration target 202 can be mounted on a flotation device 204 of the system 200. The floatation device 204 can be formed from a buoyant material. In some examples, the floatation device 204 can be formed of natural material, such as wood. In other examples, the floatation device 204 can be formed from synthetic material, such as plastic, closed cell foam, or fiberglass.

In some examples, the floatation device 204 can be implemented as a fish aggregating device (FAD). In such a situation, the floatation device 204 can be tethered to one or more anchors 206. Additionally, the floatation device 204 can be formed of multiple FADs tethered together. The anchors 206 can be implemented, for example, as concrete or metal blocks that remain relatively stationary on a floor 208 of the body of water. Each of the anchors 206 can be tethered to the floatation device 204 via a rope 210. Each rope 210 can be a predetermined length that causes the calibration target 202 to remain submerged beneath a surface 212 of the body of water by a predetermined submergence depth, marked as "S" in FIG. 4. It is noted that due to the nature of movement in the body of water (e.g., tide changes, waves, etc.), the predetermined depth may not remain constant. The predetermined submergence depth can be, for example, about 4 cm to about 1 m or possibly deeper dependent upon the clarity of the water.

In operation, the calibration target 202 can output light rays 214 that can penetrate the surface 212 of the water and reach the image sensor. As noted, the calibration target 202 can be sized and/or illuminated in a manner that the image sensor can capture a measurable quantity of light of at least 7.9 photons per every 91 meters (about 300 feet) of the distance between the image sensor and the calibration target 202 if the image sensor is traveling at a high velocity (e.g., such as in a satellite moving at a rate of about 7000 m/s). Accordingly, the output of the calibration target 202 can have a sufficient luminance to saturate at least one pixel of the image sensor.

Additionally, the calibration target 202 can be in communication with an external system (e.g., the remote controller 66 of FIG. 1). In such a situation, the external system can cause the calibration target 202 to generate light shortly (e.g., 5 minutes or less) before the image sensor can view the area that includes the system 200 to conserve power (e.g., battery power).

The system 200 can be deployed in a permanent or semi-permanent fashion. Moreover, due to the simplicity of the materials needed to implement the system 200, only minimal and infrequent maintenance, such as battery recharging/changing and/or anti-biofouling techniques may be needed. Accordingly, the system 200 can provide an efficient, cost effective system for calibrating the image sensor and/or implementing functional typing of aquatic life.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A calibration target for an image sensor comprising:
   a panel with a predetermined length and width; and
   an optical fabric overlaying a surface of the panel that generates light on a predetermined spectral band corresponding to a spectral band detectable by the image sensor spaced apart from the calibration target by a predetermined distance;
   wherein the generated light has sufficient luminance to penetrate a predetermined depth of water and to saturate at least one pixel of the image sensor, wherein the optical fabric receives light injected in a given color in a given direction and light injected in another color in another direction, wherein the image sensor observes an aggregate of the given color and the other color.

2. The calibration target of claim 1, wherein the optical fabric is a fiber optic fabric.

3. The calibration target of claim 2, further comprising:
   a lighting system that controls a color of light output by the fiber optic fabric.

4. The calibration target of claim 1, wherein the image sensor comprises a plurality of sub-image sensors, wherein each sub image sensor detects light in a respective spectral band.

5. The calibration target of claim 4, wherein the optical fabric is configured to output light in each of the respective bands detectable by each of the plurality of sub-image sensors of the image sensor.

6. The calibration target of claim 1, wherein the image sensor is implemented on a satellite.

7. The calibration target of claim 6, wherein the predetermined width and the predetermined length of the calibration target is at least 250 meters.

8. The calibration target of claim 1, wherein the image sensor is implemented on an aircraft.

9. The calibration target of claim 8, wherein the predetermined width and the predetermined length of the calibration target is at least 5 meters.

10. The calibration target of claim 1, wherein the optical fabric comprises a plurality of light emitting diodes (LEDs).

11. The calibration target of claim 1, wherein the image sensor is between 1 and 400 kilometers away from the calibration target.

12. The calibration target of claim 1, wherein the plurality of different spectral bands correspond to the color of a species of phytoplankton.

13. A system for calibrating an image sensor comprising:
    a floatation device; and
    a calibration target affixed to the floatation device, the calibration target comprising:

a plurality of panels arranged to provide a predetermined length and a predetermined width of the calibration target; and a plurality of sheets of optical fabric, wherein each of the plurality of sheets of optical fabric overlays a corresponding one of the plurality of panels, and each of the plurality of sheets of optical fabric generates light on a predetermined spectral band corresponding to a spectral band detectable by the image sensor spaced apart from the calibration target by a predetermined distance;

wherein the light generated by the plurality of sheets of optical fabric has an aggregate sufficient luminance to penetrate a predetermined depth of water and to saturate at least one pixel of the image sensor, and wherein each sheet of optical fabric receives light injected in a given color in a given direction and light injected in another color in another direction, wherein the image sensor observes an aggregate of the given color and the other color.

14. The system of claim 13, wherein the floatation device is tethered to an anchor that rests on a floor of a body of water.

15. The system of claim 14, wherein the floatation device is tethered to the anchor by a rope with a length selected to maintain submergence of the calibration target up to the predetermined depth of water.

16. The system of claim 14, wherein the predetermined depth is up to about 1 meter.

17. The system of claim 14, wherein the predetermined width and the predetermined length of the calibration target is at least 250 meters.

18. The calibration target of claim 13, wherein a given one of the plurality of sheets of optical fabric generates light in a given spectral band and another one of the plurality of sheets of the optical light generates light in another spectral band.

19. A calibration target for an image sensor comprising:
a plurality of sheets of fiber optic fabric that each generate light to provide light on a spectral band detectable by the image sensor;

wherein the generated light has sufficient luminance to penetrate one meter of water and to saturate at least one pixel of the image sensor;

wherein each sheet of fiber optic fabric receives light injected in a given color in a given direction and light injected in another color in another direction, wherein the image sensor observes an aggregate of the given color and the other color.

* * * * *